(12) United States Patent
Corbitt, Jr. et al.

(10) Patent No.: US 9,320,517 B2
(45) Date of Patent: Apr. 26, 2016

(54) TARGETING IMPLANT FOR EXTERNAL BEAM RADIATION

(75) Inventors: John D. Corbitt, Jr., Gardens, FL (US); Lori Anthony, Lake Worth, FL (US); Kishore Kumar Dass, Jupiter, FL (US)

(73) Assignee: Surgical Radiation Products, LLC, Lake Worth, FL (US)

( * ) Notice: Subject to any disclaimer, the term of this patent is extended or adjusted under 35 U.S.C. 154(b) by 739 days.

(21) Appl. No.: 13/348,965

(22) Filed: Jan. 12, 2012

(65) Prior Publication Data

US 2013/0184577 A1 Jul. 18, 2013

(51) Int. Cl.
*A61B 6/00* (2006.01)
*A61B 17/06* (2006.01)
*A61N 5/10* (2006.01)
*A61B 6/12* (2006.01)
*A61B 8/08* (2006.01)

(52) U.S. Cl.
CPC .............. *A61B 17/06* (2013.01); *A61N 5/1049* (2013.01); *A61B 6/12* (2013.01); *A61B 8/0841* (2013.01); *A61B 17/06166* (2013.01); *A61N 2005/1061* (2013.01)

(58) Field of Classification Search
CPC . A61N 2005/1024; A61N 5/00; A61N 1/406; A61N 5/10; A61N 5/1049; A61K 41/0038; A61K 47/48992; A61K 51/1282; A61B 2019/5466
USPC .................................................. 600/1, 3, 436
See application file for complete search history.

(56) References Cited

U.S. PATENT DOCUMENTS

| | | | |
|---|---|---|---|
| 3,185,299 A | 5/1965 | Trainer | |
| 3,194,239 A | 7/1965 | Sullivan | |
| 5,047,050 A | 9/1991 | Arpesani | |
| 5,628,780 A | 5/1997 | Helland et al. | |
| 5,951,590 A | 9/1999 | Goldfarb | |
| 6,007,475 A | 12/1999 | Slater et al. | |

(Continued)

FOREIGN PATENT DOCUMENTS

| | | |
|---|---|---|
| RU | 2145187 | 2/2000 |
| WO | WO02070167 | 9/2002 |

(Continued)

OTHER PUBLICATIONS

Celine Bourgier, et al., Early Side Effects of Three-Dimensional Conformal External Beam Accelerated Partial Breast Irradiation to a Total Dose of 40 GY in One Week (A Phase II Trial), Int. J. Radiation Oncology Biol. Phys., vol. 81, No. 5, pp. 1228-1235, 2011.

(Continued)

*Primary Examiner* — Charles A Marmor, II
*Assistant Examiner* — Joshua D Lannu
(74) *Attorney, Agent, or Firm* — CRGO Law; Steven M. Greenberg, Esq.; Kara A. Brotman, Esq.

(57) ABSTRACT

A radiation targeting system is provided. The system can include an introducer and an implant. The implant can be disposed within a cannula of the introducer and the implant can include a wire stem and multiple different wire branches each extending outwardly from a proximal portion of the wire stem. A radiation source can then be used to target the implant so that radiation therapy can be delivered to a patient. Optionally, a loader and a trocar can be included with the system.

4 Claims, 16 Drawing Sheets

(56) References Cited

U.S. PATENT DOCUMENTS

| | | | |
|---|---|---|---|
| 6,200,258 B1 | 3/2001 | Slater et al. | |
| 6,371,904 B1 * | 4/2002 | Sirimanne et al. | 600/3 |
| 6,426,145 B1 | 7/2002 | Moroni | |
| 6,635,082 B1 | 10/2003 | Hossainy et al. | |
| 6,666,811 B1 | 12/2003 | Good | |
| 6,746,465 B2 | 6/2004 | Diederich et al. | |
| 6,821,283 B2 | 11/2004 | Barzell et al. | |
| 7,041,047 B2 | 5/2006 | Gellman et al. | |
| 7,127,040 B2 * | 10/2006 | Sayre | A61B 19/54 378/162 |
| 7,229,417 B2 | 6/2007 | Foerster et al. | |
| 7,407,476 B2 | 8/2008 | Lubock et al. | |
| 7,497,819 B2 | 3/2009 | White et al. | |
| 7,524,274 B2 | 4/2009 | Patrick et al. | |
| 7,776,310 B2 | 8/2010 | Kaplan | |
| 7,783,336 B2 | 8/2010 | Macfarlane et al. | |
| 7,831,293 B2 | 11/2010 | Ellis et al. | |
| 7,862,496 B2 | 1/2011 | Hermann et al. | |
| 7,862,498 B2 | 1/2011 | Nguyen et al. | |
| 7,942,843 B2 | 5/2011 | Tune et al. | |
| 7,959,900 B2 * | 6/2011 | Peng | A61K 51/1255 424/1.11 |
| 2002/0095205 A1 | 7/2002 | Edwin et al. | |
| 2005/0080337 A1 | 4/2005 | Sirimanne et al. | |
| 2005/0080338 A1 | 4/2005 | Sirimanne et al. | |
| 2005/0171428 A1 | 8/2005 | Fichtinger et al. | |
| 2007/0038014 A1 | 2/2007 | Cox et al. | |
| 2007/0238983 A1 * | 10/2007 | Suthanthiran et al. | 600/424 |
| 2008/0033286 A1 | 2/2008 | Whitmore et al. | |
| 2008/0234572 A1 | 9/2008 | Jones | |
| 2008/0281388 A1 | 11/2008 | Corbitt et al. | |
| 2009/0018636 A1 * | 1/2009 | Gailloud et al. | 623/1.11 |
| 2009/0087380 A1 | 4/2009 | Fasching et al. | |
| 2009/0216115 A1 * | 8/2009 | Seiler | A61B 19/54 600/426 |
| 2009/0275793 A1 | 11/2009 | Black et al. | |
| 2010/0099939 A1 | 4/2010 | Sutton et al. | |
| 2010/0222672 A1 | 9/2010 | Macfarlane et al. | |
| 2011/0004094 A1 | 1/2011 | Stubbs et al. | |
| 2012/0179027 A1 | 7/2012 | Suthanthiran et al. | |

FOREIGN PATENT DOCUMENTS

| | | |
|---|---|---|
| WO | WO2007075241 | 7/2007 |
| WO | WO2010126949 | 11/2010 |
| WO | WO2011085034 | 7/2011 |

OTHER PUBLICATIONS

Tanya S. Berrang, et al., Three-Year Outcomes of a Canadian Multicenter Study of Accelerated Partial Breast Irradiation Using Conformal Radiation Therapy, Int. J. Radiation Oncology Biol. Phys., vol. 81, No. 5, pp. 1220-1227, 2011.

Fiducial Markers: Guide & Procedure Based Recommendations, CIVCO Medical Solutions, "Breast," 2012, p. 3.

Program—Radiation Therapy: Emerging Breast Treatment & RT, Winter 2009, photo caption at p. 8.

* cited by examiner

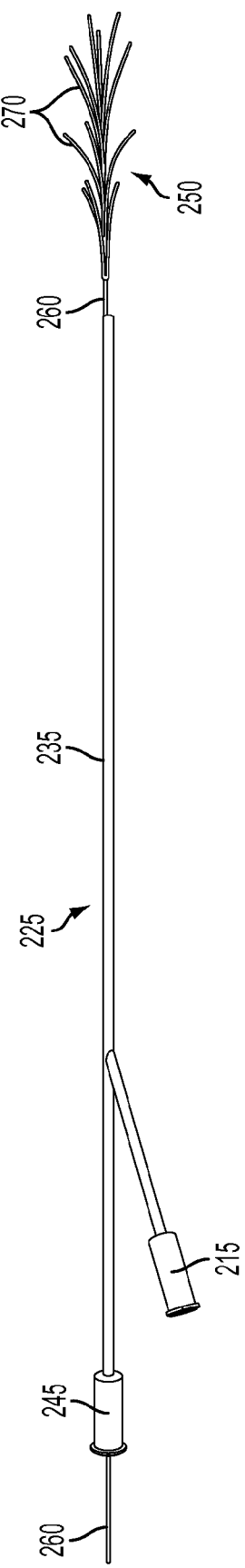

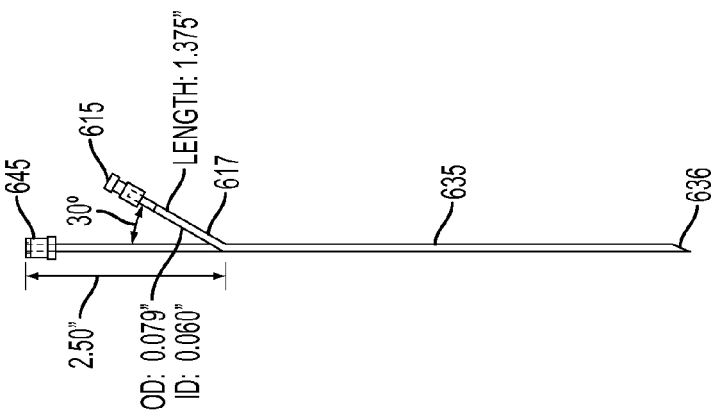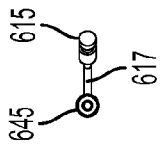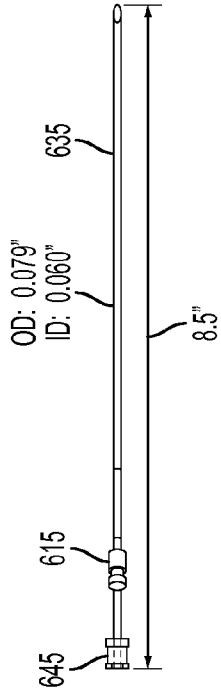

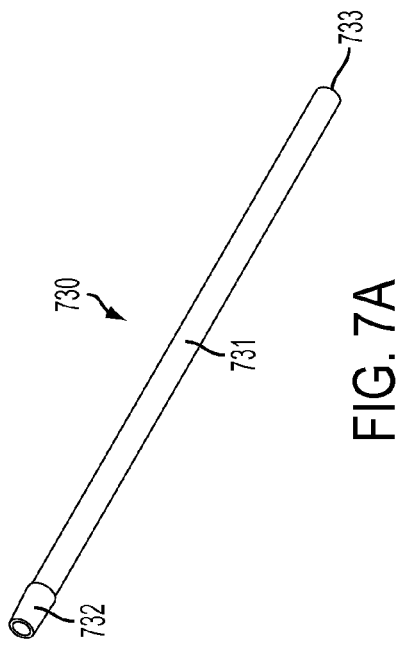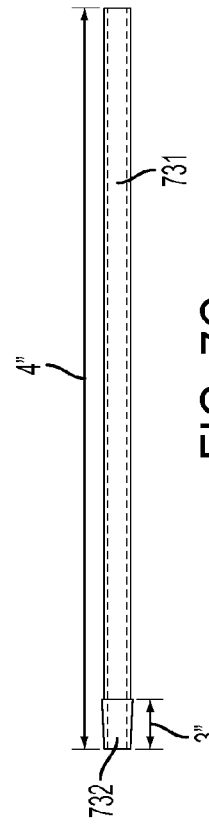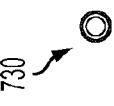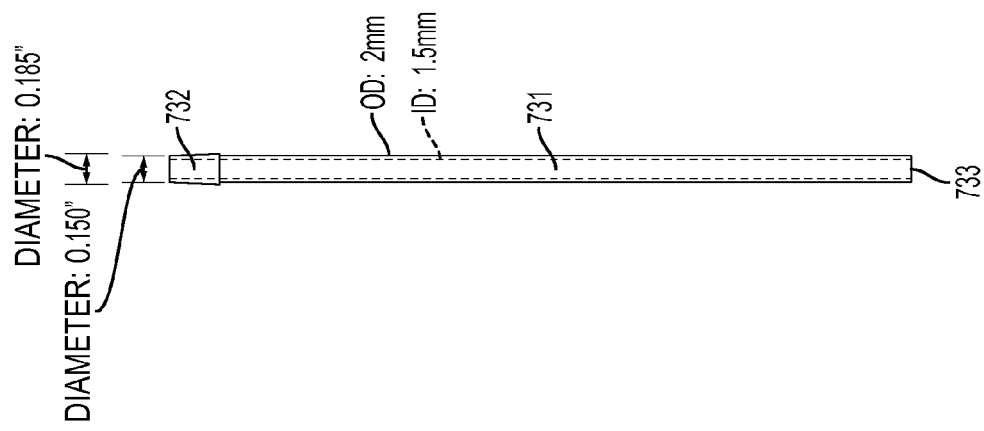

TARGETING IMPLANT FOR EXTERNAL BEAM RADIATION

BACKGROUND OF THE INVENTION

1. Field of the Invention

The present invention relates to a medical device and more particularly to an in-vivo medical device for use during external beam radiation therapy (EBRT).

2. Description of the Related Art

Radiation for breast cancer is most often accomplished by the use of full breast radiation. This imparts radiotherapy to the entire area of the breast. Radiation of the breast will necessarily involve surrounding structures such as, but not limited to, the heart, lungs, esophagus, chest wall, ribs and other structures that are in close proximity to the breast. Thus, a new concept of only partial breast radiation has grown in popularity and involves the use of balloon catheters to treat cancer in the lumpectomy cavity. Studies thus far indicate that it is as effective as full breast radiation and eliminates damage to the surrounding organs.

Partial breast radiation is currently being delivered through balloon catheters placed into the lumpectomy cavity at the time of surgery or later under ultrasound guidance. This process of using a balloon catheter for radiation treatment involves placing a radioactive seed or source down the indwelling catheter for a brief period of time. Unfortunately, this method of utilizing a catheter and radioactive seed has a number of drawbacks. For instance, utilizing a concentrated dose of radiation over a short period of time in the form of a radioactive seed planted through means of the catheter creates a multitude of side effects such as fat necrosis, seromas, hematomas, infection and undesirable cosmetic outcomes. The use of partial breast radiation balloon catheters also requires additional expensive equipment to maintain and direct the source of the radiation into the partial breast balloon catheter, which is not available at all radiation sites.

Currently, the other source of breast radiation is full breast radiation by external beam equipment. The external beam radiation equipment is excellent for solid organs such as the liver that contains a small tumor or the head of the pancreas that contains a small tumor. These tumors are most effectively treated with external beam radiation by placing a target or a metallic marker into the area of the tumor, which allows the external beam to be focused on this tumor and avoid damage to the surrounding tissue. These solid organs are rigid and do not move during the radiation treatment. But the breast is an external structure, consisting primarily of fatty tissue, unlike the liver and pancreas.

Of note, the use of metallic markers in the breast tissue creates an unstable environment for the marker, and the marker does not necessarily remain in place or in a constant location. Consequently, in fatty tissue, these small seeds or targets may move from the intended target site, rendering the therapy ineffective. Thus, in order to utilize external beam radiation on the breast, a stable target must be available.

BRIEF SUMMARY OF THE INVENTION

Embodiments of the present invention address deficiencies of the art in respect to radiation treatments for cancer and provide a new and novel system for delivering radiation to a target. In an embodiment of the invention, a radio-opaque implant can be disposed within the cannula of an introducer. The radio-opaque implant can include a wire stem and multiple different wire branches each extending outwardly from a proximal portion of the wire stem towards the proximal portion of the wire stem. The system can further include a trocar and a loader.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIG. 2 is a perspective view of another embodiment of a radiation targeting system;

FIG. 6A is an isometric view of one embodiment of an introducer 625 for use in a radiation targeting system of the present invention;

FIG. 6B is a top view of the introducer of FIG. 6A;

FIG. 6C is a side view of the introducer of FIG. 6A;

FIG. 6D is a front view of the introducer of FIG. 6A;

FIG. 7A is an isometric view of a loader for use in a radiation targeting system of the present invention;

FIG. 7B is a top view of the loader of FIG. 7A;

FIG. 7C is a side view of the loader of FIG. 7A;

FIG. 7D is a front view of the loader of FIG. 7A;

DETAILED DESCRIPTION OF THE INVENTION

Embodiments of the invention provide for a radiation targeting system used during external beam radiation therapy (EBRT) that can be delivered though a multi-directional stereotactic radiation source. The radiation targeting system can include an introducer with an implant disposed within the introducer. The implant can further include a wire stem with multiple different wire branches extending from the wire stem. In this way, the implant can be a target for EBRT for organs that are composed of primarily fatty tissue, such as the breast, where a stable environment for placement of a non-moving target is needed. In addition, the implant can be inserted into the breast at the time of a lumpectomy, but radiation can be delayed. Of further note, the radiation targeting system can be used to aspirate the lumpectomy cavity causing it to collapse and conform to the size and shape of the implant. In this way, the implant shape may guide the external beam source in order to target a more specific area of the cavity. In addition, with cavity collapse, there is a decrease in hematoma, seroma, and other defects within the site of the lumpectomy to develop due to the use of an external radiation source opposed to a concentrated internal seed in close proximity to the tissue in the cavity.

Figure 1:
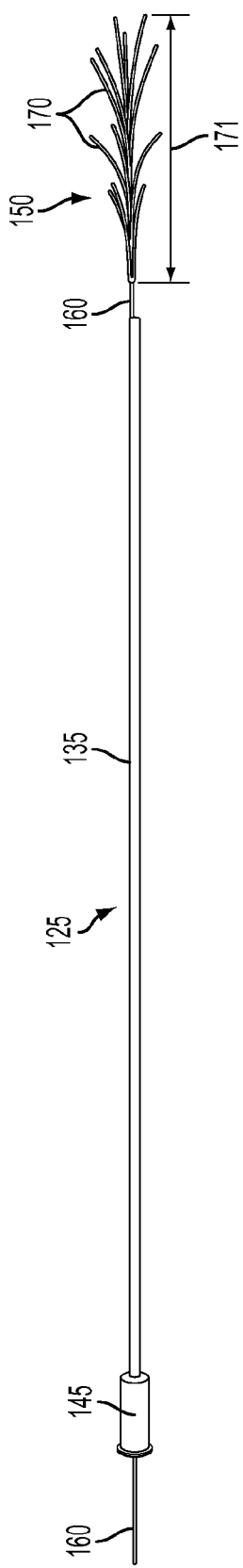
FIG. 1 is a perspective view of one embodiment of a radiation targeting system.

In illustration, FIG. 1 is a perspective view of one embodiment of a radiation targeting system. The system can comprise an introducer 125 and an implant 150. The introducer 125 can include a cannula 135. On one end of the cannula 135 can be a port 145. The implant 150 can be disposed within the cannula 135 of the introducer 125 and can include a wire stem 160 and multiple different wire branches 170, each extending outwardly from a proximal portion 171 of the wire stem 160 towards the proximal portion 171 of the wire stem 160. The implant 150 can be radio-opaque and may or may not be biodegradable. Both the introducer 125 and the implant 150 can be manufactured by any technique now known or later developed. In addition, both the introducer 125 and the implant 150 can be made of any metallic material, suitably sterilized, or other biocompatible material, including but not limited to stainless steel, gold, ceramic, titanium, and nickel titanium.

If further illustration, FIG. 2 is a perspective view of another embodiment of a radiation targeting system, which can include an introducer 225 comprising a cannula 235. The cannula 235 can include a port 245 at one end and an aperture in which an implant 250 can be inserted into the port 245 of the introducer 225. The introducer 225 can also include a side port 215. The side port 215 can be used to introduce fluids, such as saline, or to aspirate fluid or air from a lumpectomy cavity. Of note, in this way, by aspirating any fluid or air from the cavity, the tissue surrounding the cavity can collapse around the implant 250 and conform to the size and shape of the implant 250. The implant 250 can comprise a wire stem 260 and multiple different wire branches 270.

Figure 3A:
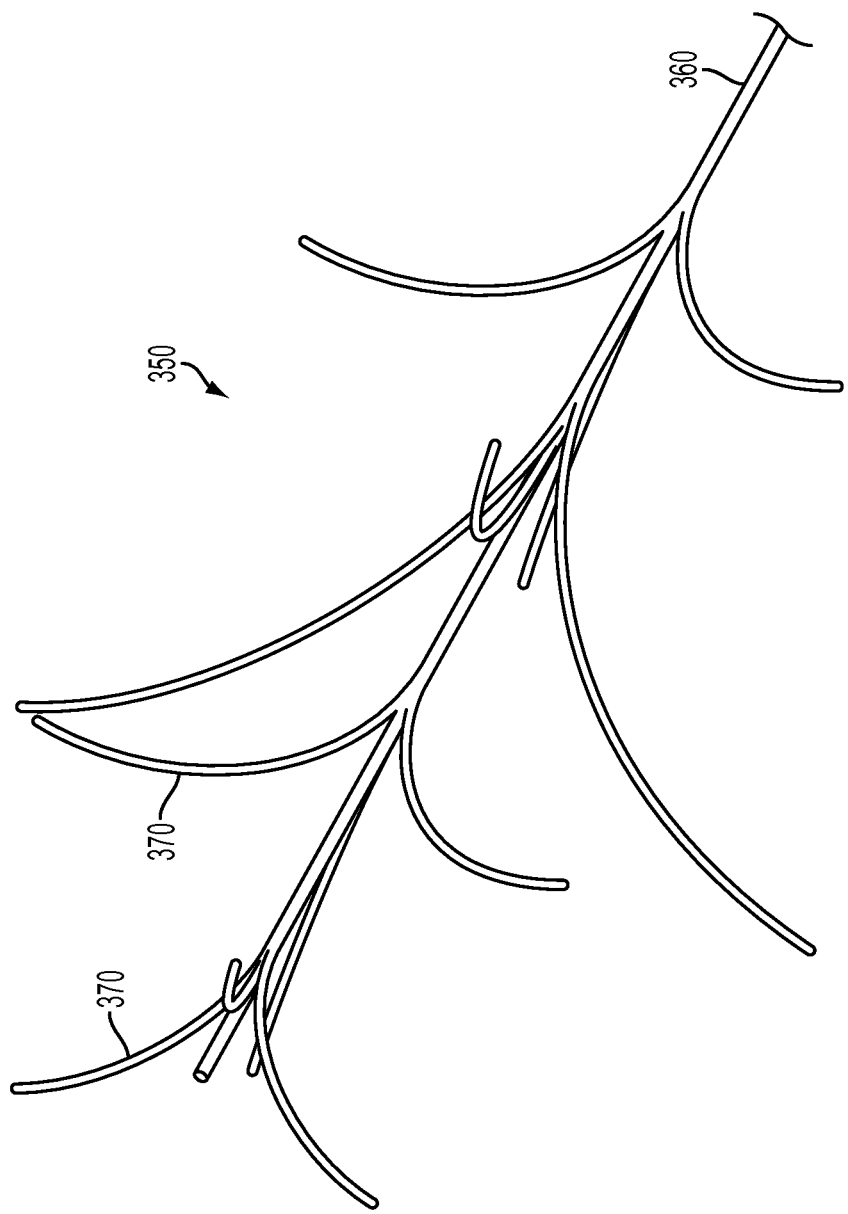
FIG. 3A is an isometric view of one embodiment of an implant for use in a radiation targeting system of the present invention.

In yet further illustration, FIG. 3A is an isometric view of one embodiment of an implant 350 for use in a radiation targeting system of the present invention. The implant 350 can be radio-opaque and can comprise a wire stem 360 and multiple different wire branches 370, each extending outwardly from a proximal portion of the wire stem 360 towards the proximal portion of the wire stem 360. Of note, the wire branches 370 can be arched. Of further note, an implant 350 can be manufactured in a variety of size and shapes. In addition, an implant 350 is not limited to a specific number of wire branches 370, for instance, there can be one wire branch 370 that is helical-shaped, multiple wire branches 370 that are spherical-shaped, multiple wire branches 370 that are helical-shaped, etc. Optionally, the implant 350 can include growth stimulators and/or stem cells. In addition, the implant 350 can be treated in any way now known or later developed so that tissue does not stick to it; in one instance, the implant 350 can be highly polished. Of note, the implant 350 can be placed, with or without an introducer, in the body during surgery (following a lumpectomy or other procedure) or after any procedure using ultrasound guidance.

Figure 3B:
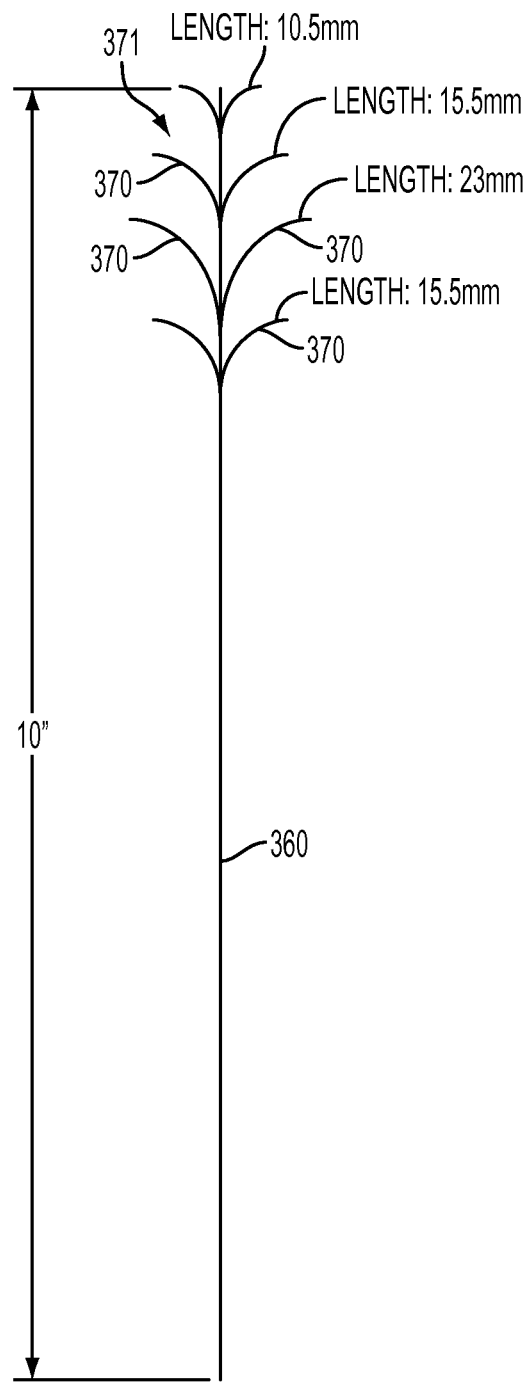
FIG. 3B is a top view of the implant of FIG. 3A.

In even further illustration, FIG. 3B is a top view of the implant 350 of FIG. 3A. At a proximal portion 371 of a wire stem 360, multiple wire branches 370 can extend outwardly. As illustrated in FIG. 3B, the implant can be ten inches in length with a first set of branches comprising a length of at least ten and one-half millimeters, a second and fourth set of branches comprising a length of at least fifteen and one-half millimeters, and a third set of branches comprising a length of twenty three millimeters.

Figure 3C:
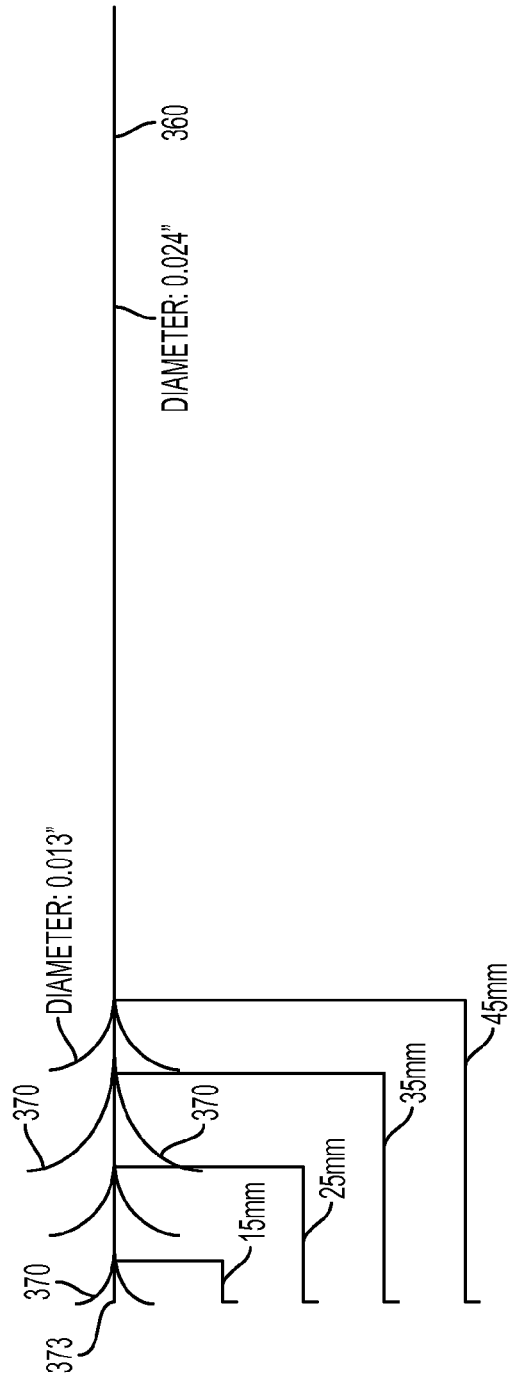
FIG. 3C is a side view of the implant of FIG. 3A.

In even yet further illustration, FIG. 3C is a side view of the implant 350 of FIG. 3A. The wire stem 360 can have a diameter of at least 0.024 inches and the multiple different wire branches 370 can have a diameter of at least 0.013 inches. The wire branches 370 can be coupled to the wire stem 360 at a variety of distances; in one instance, the distance from a tip 373 of the wire stem 360 to a first set of branches can be at least fifteen millimeters, from the tip 373 to a second set of branches can be at least twenty five millimeters, from the tip 373 to a third set of branches can be at least thirty five millimeters, and from the tip 373 to a fourth set of branches can be at least forty five millimeters. Of note, the wire branches 370 can be attached to the wire stem 360 by any method now known or later developed, including but not limited to welding and crimping. Of further note, individual wire branches 370 can be directly coupled to the wire stem 360 or individual wire branches 370 can be grouped together to form sets of wire branches 370, which can then be attached to the wire stem 360 using any method now known or later developed. In one instance, four individual wire branches 370 can form a set of wire branches 370 and there can be four sets of wire branches 370 coupled to the wire stem 360.

Figure 3D:
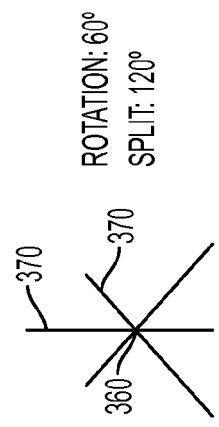
FIG. 3D is a front view of the implant of FIG. 3A.

FIG. 3D is a front view of the implant 350 of FIG. 3A. Wire branches 370 can be positioned around a wire stem 360 so that there is about a sixty degree rotation between each wire branch 360. In addition, there can be a split of about one hundred twenty degrees.

Figure 4A:
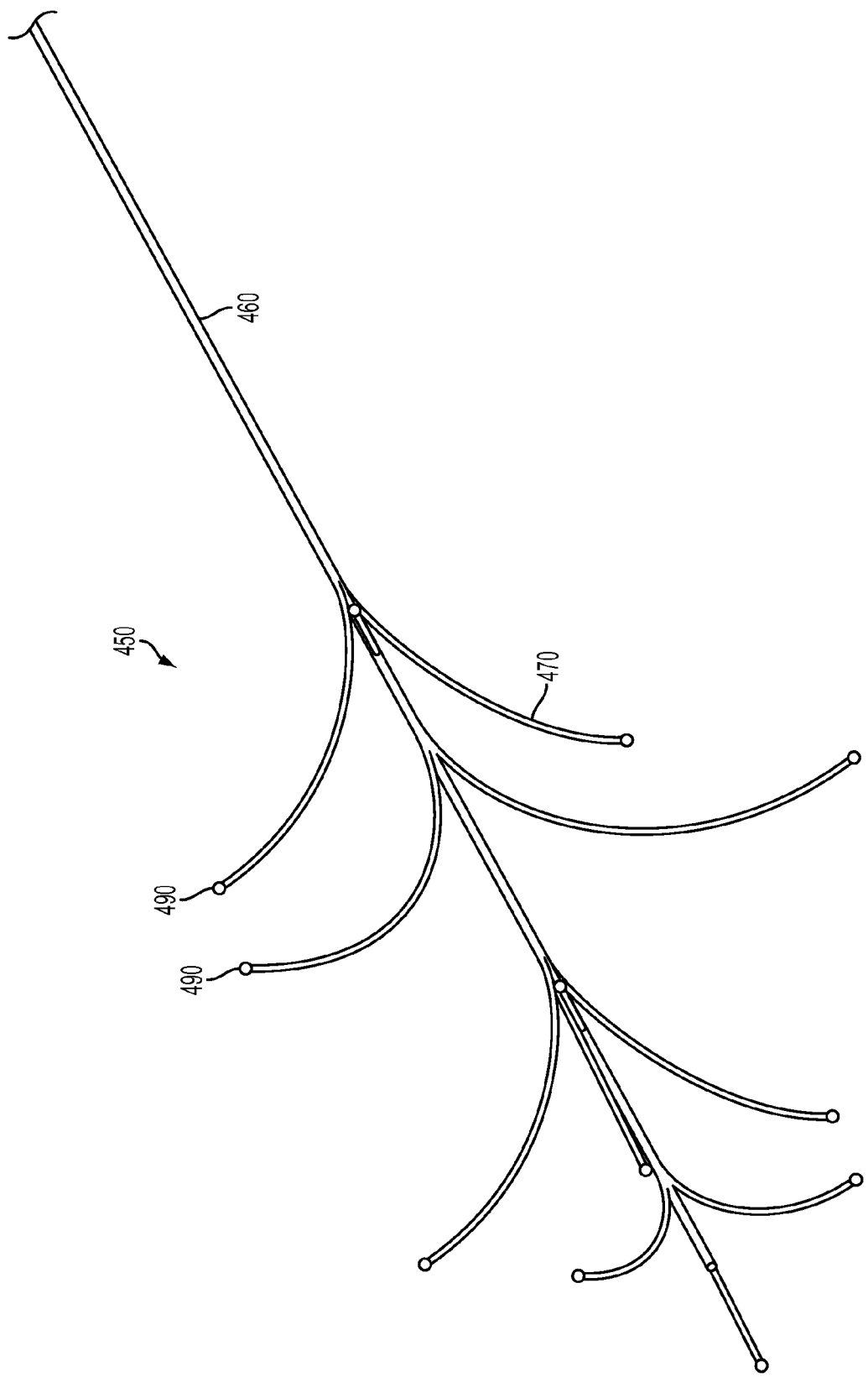
FIG. 4A is an isometric view of another embodiment of an implant for use in a radiation targeting system of the present invention.

In further illustration, FIG. 4A is an isometric view of another embodiment of an implant 450 for use in a radiation targeting system of the present invention. The implant 450 can be radio-opaque and can comprise a wire stem 460 and multiple different wire branches 470, each extending outwardly from a proximal portion of the wire stem 460 towards the proximal portion of the wire stem 460. Coupled to one end of at least one wire branch 470 can be a marker 490. Of note, the marker 490 is not limited to attachment at an end of each wire branch 470. In addition, a marker 490 does not need to be coupled to every wire branch; a marker 490 can be coupled to all wire branches 480, one, or somewhere in between. The marker 490 is not limited to a specific size or shape; for instance the marker 490 can be a non-radioactive seed, which can be made from any radio-opaque material, including but not limited to gold and titanium. The marker 490 can also be round, like a ball. Of note, multiple different marker materials can be contained within an implant 450; for instance, an implant 450 may be comprised of a nickel titanium wire stem 460 and wire branches 470 with gold seeds coupled to the ends of the wire branches 470. Of further note, the wire branches 470 can be arched. Of even further note, an implant 450 can be manufactured in a variety of size and shapes. In addition, an implant 450 is not limited to a specific number of wire branches 470, for instance, there can be one wire branch 470 that is helical-shaped, multiple wire branches 470 that are spherical-shaped, multiple wire branches 470 that are helical-shaped, etc. Optionally, the implant 450 can include growth stimulators and/or stem cells. In addition, the implant 450 can be treated in any way now known or later developed so that tissue does not stick to it; in one instance, the implant 450 can be highly polished.

Figure 4B:
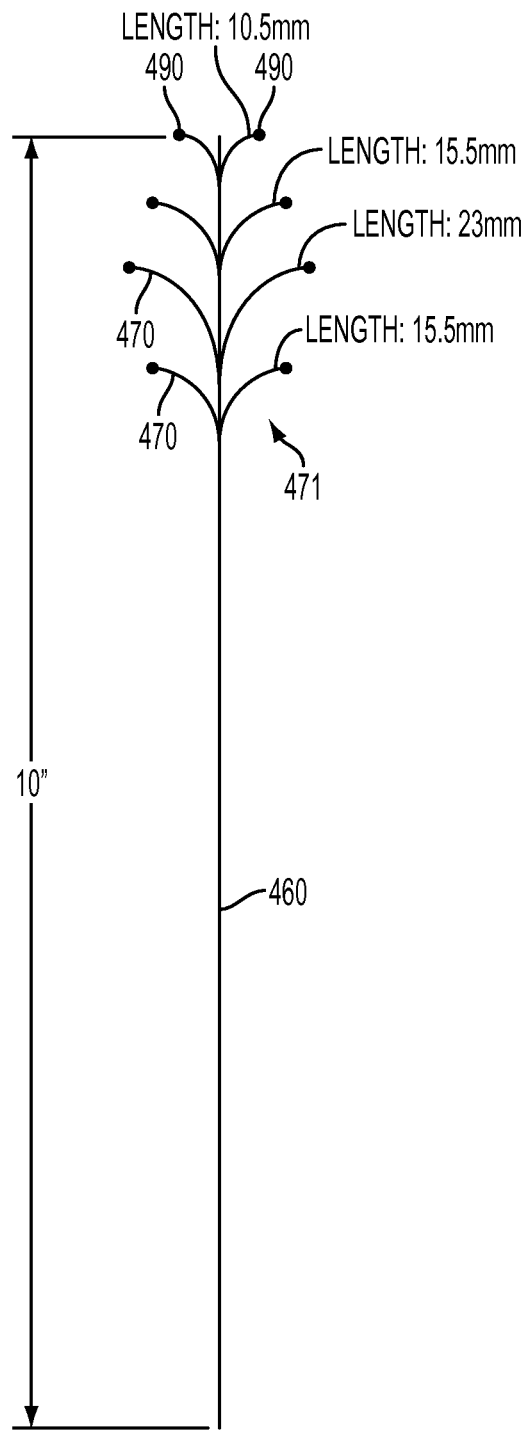
FIG. 4B is a top view of the implant of FIG. 4A.

In yet even further illustration FIG. 4B is a top view of the implant 450 of FIG. 4A. At a proximal portion 471 of a wire stem 460, multiple wire branches 470 can extend outwardly. The wire stem 460 can be at least ten inches in length and can have a diameter of at least 0.024 inches. As illustrated in FIG. 4B, the implant can have a first set of branches comprising a length of at least ten and one-half millimeters, a second and fourth set of branches comprising a length of at least fifteen and one-half millimeters, and a third set of branches comprising a length of twenty three millimeters. In addition, a marker 490 can be coupled to one end of at least one wire branch 470; in other words, a marker 490 does not need to be coupled to each wire branch 470.

Figure 4C:
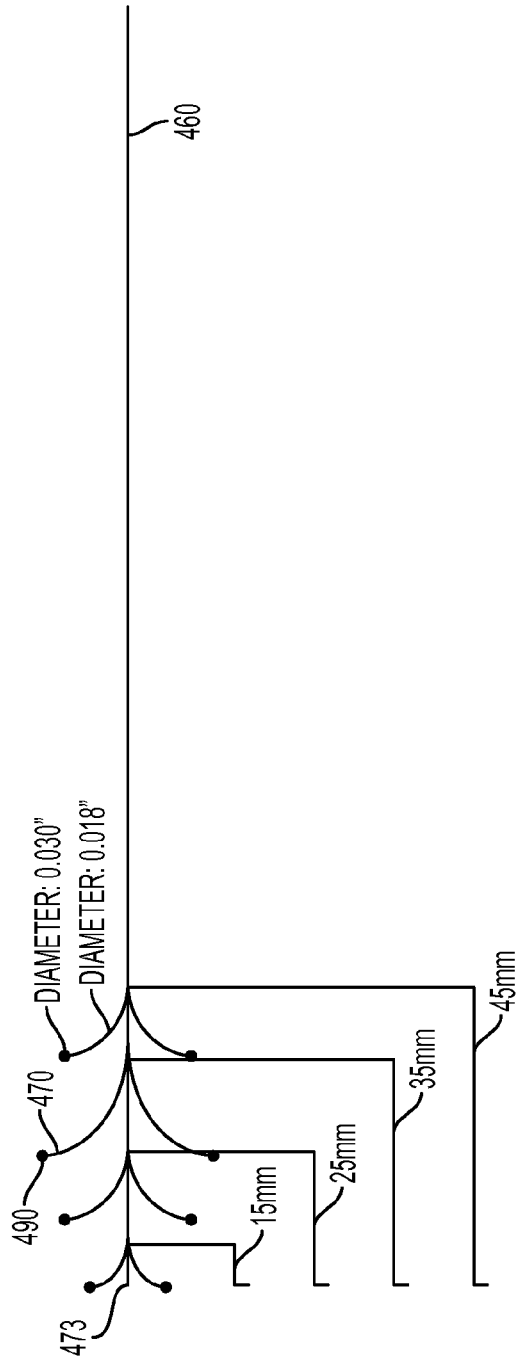
FIG. 4C is a side view of the implant of FIG. 4A.

FIG. 4C is a side view of the implant 450 of FIG. 4A. The multiple different wire branches 470 can have a diameter of at least 0.018 inches. A marker 490 can be coupled to the wire branch 470; the marker 490 can be of any shape and size; in one embodiment, the marker 490 can be a ball with a diameter of at least 0.030 inches. In another embodiment, the marker 490 can be a non-radioactive seed. The wire branches 470 can be coupled to the wire stem 460 at a variety of distances; in one instance, the distance from a tip 473 of the wire stem 460 to a first set of branches can be at least fifteen millimeters, from the tip 473 to a second set of branches can be at least twenty five millimeters, from the tip 473 to a third set of branches can be at least thirty five millimeters, and from the tip 473 to a fourth set of branches can be at least forty five millimeters. Of note, the wire branches 470 can be attached to the wire stem 460 by any method now known or later developed, including but not limited to welding and crimping. Of further note, individual wire branches 470 can be directly coupled to the wire stem 460 or individual wire branches 470 can be grouped together to form sets of wire branches 470, which can then be attached to the wire stem 460 using any method now known or later developed. In one instance, four individual wire branches 470 can form a set of wire branches 470.

Figure 4D:
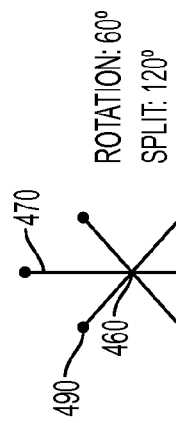
FIG. 4D is a front view of the implant of FIG. 4A.

In yet even further illustration, FIG. 4D is a front view of the implant 450 of FIG. 4A. Wire branches 470 can be positioned around a wire stem 460 so that there is about a sixty degree rotation between each wire branch 460. Attached to at least one of the wire branches 460 can be a marker 480. In addition, there can be a split of about one hundred twenty degrees.

Figure 5:
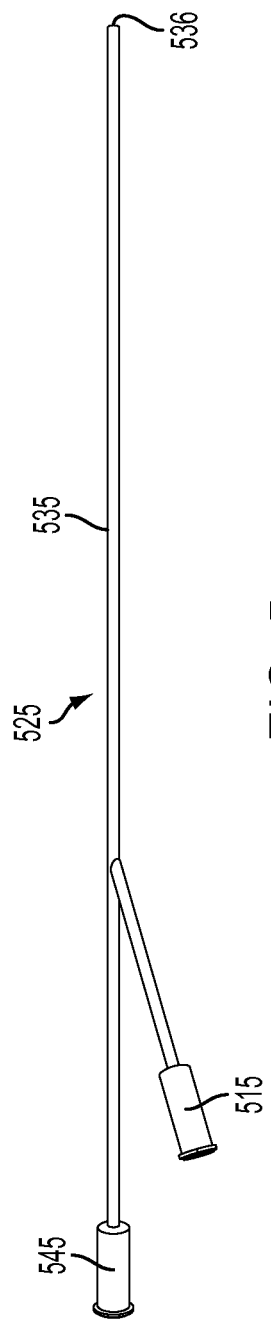
FIG. 5 is a perspective view of one embodiment of an introducer for use in a radiation targeting system of the present invention.

In further illustration FIG. 5 is a perspective view of one embodiment of an introducer 525 for use in a radiation targeting system of the present invention. The introducer 525 can be comprised of a cannula 535. On one end of the cannula 535 can be a port 545 and on the opposite end of the cannula 535 can be an aperture 536. Of note, in use, it is generally the end of the cannula 535 with the aperture 536 that enters a body to enable an implant to be placed within the body. An implant can be disposed within the cannula 535 of the introducer 525. An implant can also be adapted for insertion into a port 545 of the introducer 525. A side port 545 can also coupled to the cannula 535. Of note, in one instance, the cannula 535 can be bifurcated, where one port 545 is coupled to one part of the bifurcation fork and a side port 515 is coupled to a second part of the bifurcation fork. In another instance, a tube can be coupled to the cannula 535 and the side port 515 can be coupled to the end of the tube not attached to the cannula 535. In either case, a channel is maintained between the fork where the side port 515 is coupled and the cannula 535 to allow materials to pass, including but not limited to air, fluid, and medical instruments. Of further note, the introducer 525 can be made of any metallic material, suitably sterilized, or other biocompatible material, including but not limited to stainless steel, gold, ceramic, titanium, and nickel titanium In further illustration, FIG. 6A is an isometric view of one embodiment of an introducer 625 for use in a radiation targeting system of the present invention. The introducer 625 can include a cannula 635. The cannula 635 can include a port 645 at one end of the cannula 635 and an aperture 636 at an opposite end of the cannula 635. The port 645 can include a locking apparatus, for instance a lever lock, which can secure an instrument to the introducer 625; for instance, a trocar can be instructed through the port 645 and secured in place to the introducer 625. More specifically, the trocar can contain a male component on one end that can be screwed into a female component on the port 645, thus securing the trocar in the introducer 625. Optionally, a side port 615 can be coupled to a tube 617, which can be coupled to the cannula 635 of the introducer 625. The tube 617 can be coupled to the cannula 635 using any method now known or later developed, including but not limited to welding. In addition, the cannula 635 with the coupled tube 617 can be manufactured as one piece. The side port 615 can include a seal. In this way, an instrument can be coupled to the seal so as to aspirate air or fluid from a cavity. In addition, an instrument can be coupled to the side port 615, with or without a seal, which can introduce fluids into the cavity or into a component, for instance a balloon, attached to an implant or the introducer 625. The side port 615 can also include a locking apparatus. The introducer 625 can be made from any metallic material, suitably sterilized, or other biocompatible material, including but not limited to stainless steel, gold, ceramic, titanium, and nickel titanium In yet further illustration, FIG. 6B is a top view of the introducer 625 of FIG. 6A. The introducer can include a cannula 635 coupled to a tube 617. The tube 617 can have a length of at least 1.375 inches and can have an inner diameter of at least 0.060 inches and an outer diameter of at least 0.079 inches. A side port 615 can be coupled to on one end of the tube 617. In addition, the distance from the attachment point between the tube 617 and the cannula 635 to the end of a port 645 coupled to one end of the cannula can be at least two and one-half inches. Also, the angle between the cannual 635 and the tube 617 can be at least thirty degrees. The cannula 635 can include an aperture 636 at an opposite end of the port 645. Of note, the end of the cannula 635 defining the aperture 636 can be pointed or can be flat; in other words, the end of the cannula 635 can be sharp in order to make an opening in skin so that an implant can be introduced to the body or the end of the cannula 635 can be dull requiring another instrument, such as a trocar, be used, whether or not in conjunction with the introducer.

FIG. 6C is a side view of the introducer 625 of FIG. 6A. The introducer 635 can include a cannula 635 having a length of at least eight and one-half inches and an inside diameter of 0.060 inches and an outer diameter of 0.070 inches. Attached to the cannula 635 on one end can be a port 645. A side port 615 can also be coupled to the cannula 635.

In yet even further illustration, FIG. 6D is a front view of the introducer 635 of FIG. 6A showing a port 645 and a side port 615 coupled to a tube 617.

In further illustration, FIG. 7A is an isometric view of a loader 730 for use in a radiation targeting system of the present invention. The loader 730 can include a tube 731 with an aperture 733 at one end of the tube 731 and a tip 732 at an opposite end of the tube 731. The loader 730 can be made of any material now known or later developed, including but not limited to stainless steel, ceramic, and titanium. Of note, the tip 732 can include an outer diameter that tapers from a distal end of the tip 732 with a diameter smaller than a diameter of the cannula of the introducer, towards the opposite end of the tip 732 with a diameter that is equal to or greater than the diameter of the cannula of the introducer. In use, the loader 730 can be used to load the implant into the introducer. Of note, if the optional loader 730 is used, a portion of the implant remains on the outside of the loader 730; in other words, only a portion of the implant is inserted into the loader 730.

In further illustration, FIG. 7B is a top view of the loader 730 of FIG. 7A. A tube 731 can have an inner diameter of at least one and one-half millimeters and an outer diameter of at least two millimeters. The tube 731 can include an aperture 733 on one end and at an opposite end a tip 732. The tip 732 can include an inner diameter of at least 0.150 inches. The tip 732 can also include an outer diameter of at least 0.150 at a distal end of the tip 732 that tapers to a diameter smaller than a diameter of the cannula of the introducer towards the opposite end of the tip 732 with a diameter that is equal to or greater than the diameter of the cannula of the introducer. In this way, the loader 730 is adapted to fit into the port of the introducer and because of the size difference between the tapering of the outer diameter of the loader and the inner diameter of the port of the introducer, the loader is stop from moving further into the port of the introducer; this allows the implant to be inserted through the port of the introducer into the cannula of the introducer.

FIG. 7C is a side view of the loader 730 of FIG. 7A illustrating that the loader can be at least four inches in length with the tip 732 having a length of 0.3 inches, thus making the length of the tube 731 about 3.7 inches.

In yet even further illustration, FIG. 7D is a front view of the loader 730 of FIG. 7A.

Figure 8:
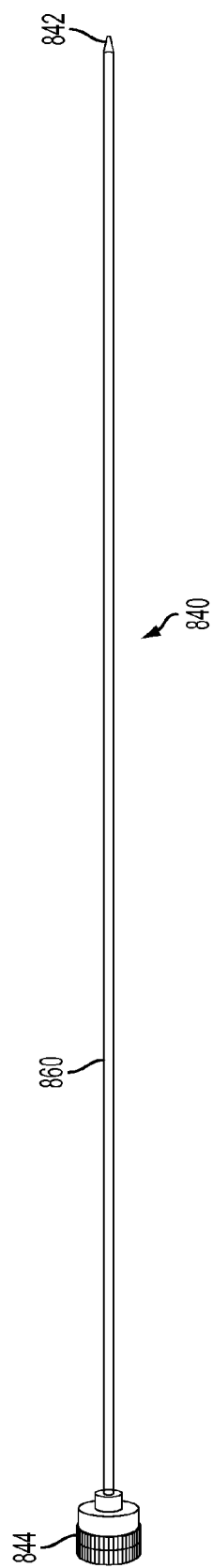
FIG. 8 is a perspective view of a trocar for use in a radiation targeting system of the present invention.

In further illustration, FIG. 8 is a perspective view of a trocar 840 for use in a radiation targeting system of the present invention. The trocar 840 can include a wire stem 860 with a tip 842 at one end and a top 844 at an opposite end of the wire stem 860. Of note, the top 844 can be locking so as to securely attach to a port of an introducer. In other words, the trocar 840 can include a male locking component that locks into a female receiver on the introducer. Of note, the female receiver can be part of the port on the introducer. The trocar 840 can be of any length so that it can be inserted into the introducer of the radiation targeting system; the trocar 840 is adapted for insertion through the cannula of the introducer. The trocar 840 can be made of any material now known or later developed, including but not limited to stainless steel, ceramic, and titanium. Of note, the trocar 840 would normally not be used if an implant is placed, using an introducer, in a body during surgery, though a trocar 840 would like be used when placing the implant using ultrasound guidance post operation.

Figure 9A:
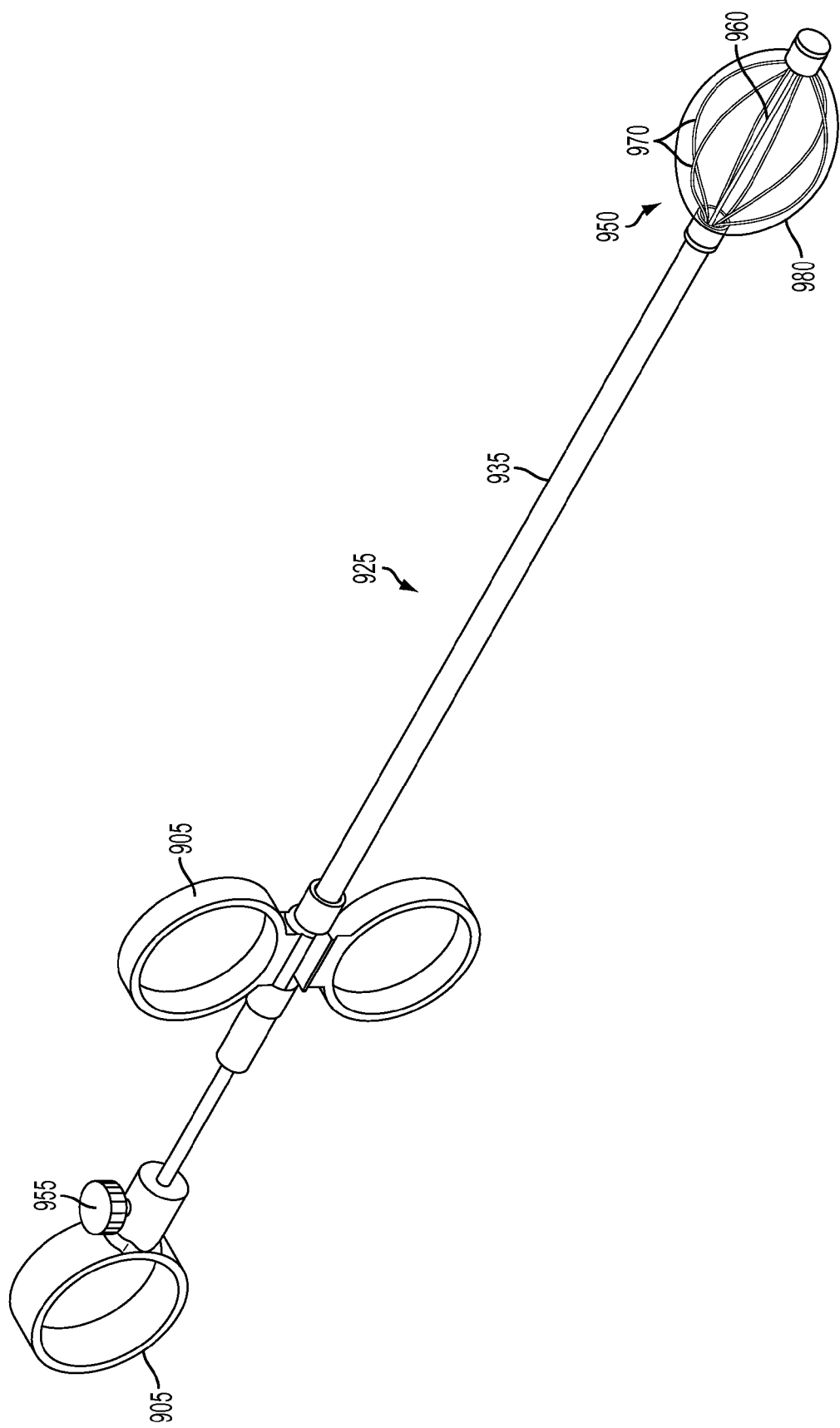
FIG. 9A is a perspective view of one embodiment of a radiation targeting system.
Figure 9B:
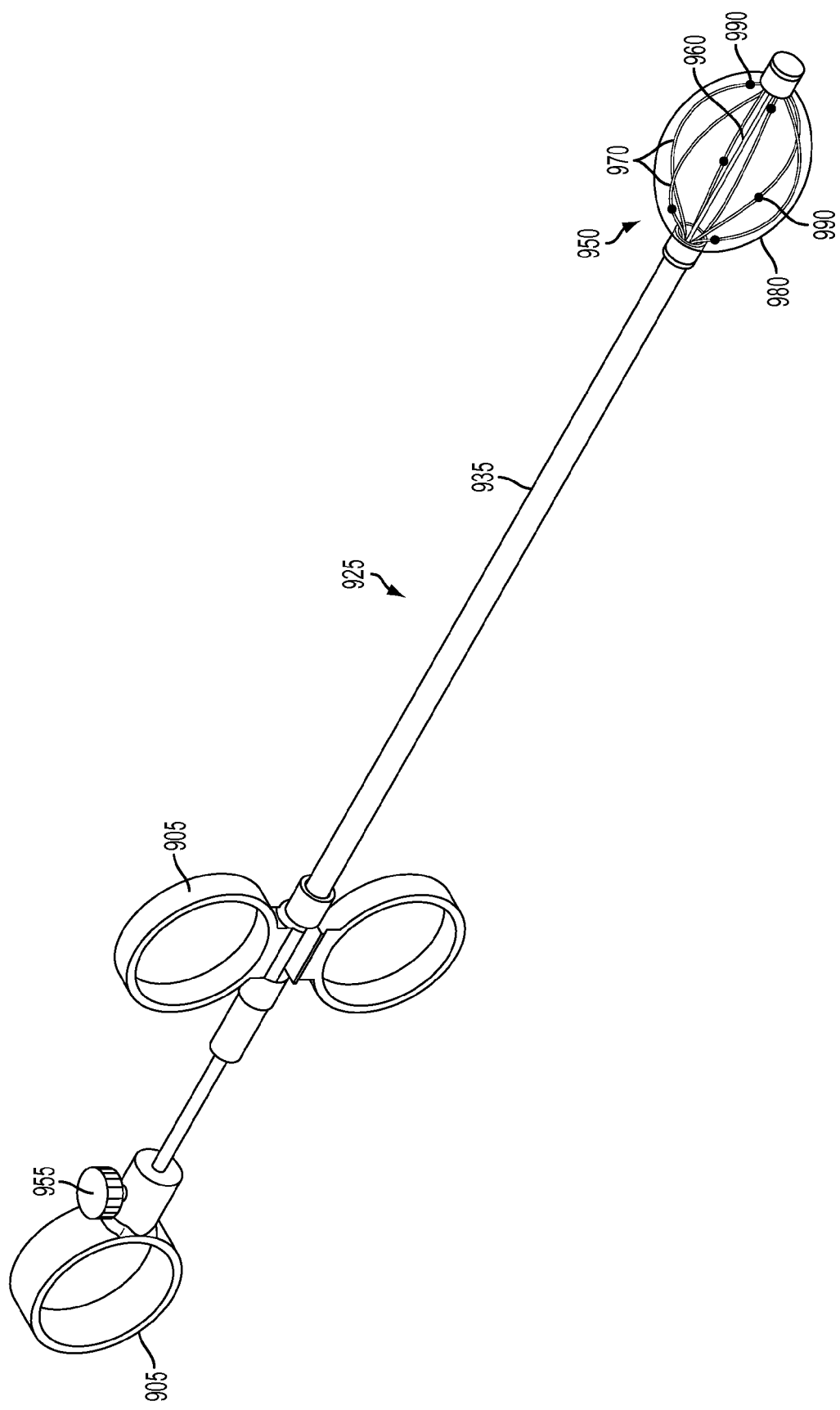
FIG. 9B is a perspective view of another embodiment of a radiation targeting system.

In even further illustration, FIGS. 9A and 9B are each perspective views of embodiments of a radiation targeting system that can include an introducer 925 that can further include a cannula 935. The introducer 925 can include a plurality of finger rings 905 and a valve 955. The valve 955 can be used to inflate a balloon 980. The balloon 980 can be coupled to a plurality of wire branches 970 and a wire stem 960. In other words, there can be at least two wire branches 970. Optionally, the wire branches 970 can be coupled to at least one marker 990, as shown in FIG. 9B. The marker 990 can be coupled to each and every wire branch 970, just one wire branch 970, or somewhere in between. In addition, the marker 990 can be coupled anywhere on the wire branch 970; for instance, the marker 990 can be coupled toward an end of the wire branch 970, in the middle of the wire branch 970, or somewhere in between. Also, there can be multiple markers 990 on each wire branch 970, no marker 990 on a wire branch 970, or any combination thereof. For instance, if there are a total of eight wire branches 970, there may be one marker 990 on four wire branches 970, no marker on two wire branches 970, and two markers 990 on the remaining two wire branches 970. A marker 970 is not limited to a specific size or shape; for instance the marker 970 can be a non-radioactive seed, which can be made from any radio-opaque material, including but not limited to ceramic, gold, and titanium. The marker 990 can also be round, like a ball. The balloon 980, the wire branches 970, the wire stem 960, and the marker 990, if present, can be components of an implant 950 in an embodiment of a radiation targeting system. Further, the balloon 980, the wire branches 970, the wire stem 960, and the marker 990 can each be any size (length, diameter, width, etc.). Of further note, the balloon 980 can provide support to a lumpectomy cavity. In addition, the balloon 980 can be coated with a material to prevent tissue from "sticking" to the balloon 980.

Figure 10A:
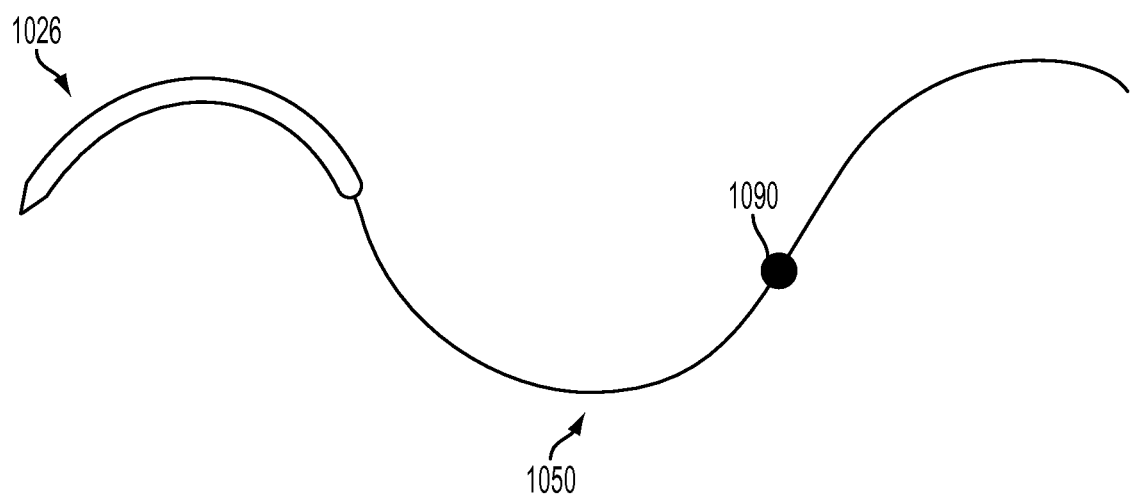
FIG. 10A is a line drawing of one embodiment of an implant for use in a radiation targeting system of the present invention.
Figure 10B:
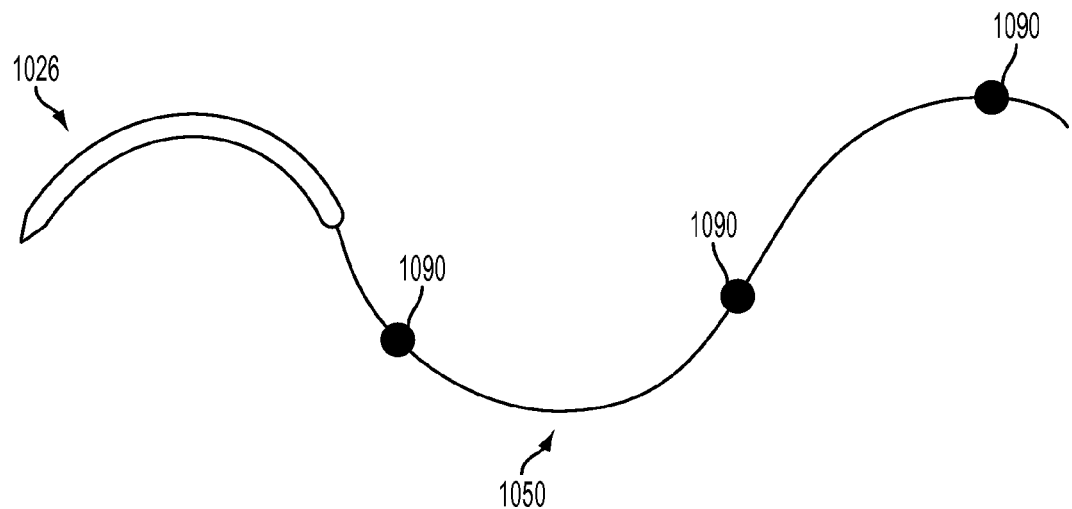
FIG. 10B is a line drawing of one embodiment of an implant for use in a radiation targeting system of the present invention; and, FIG. 10C is a line drawing of one embodiment of an implant for use in a radiation targeting system of the present invention.

In yet even further illustration, FIGS. 10A and 10B are line drawings of embodiments of implants 1050 for use in a radiation targeting system of the present invention can include a needle 1026 coupled to an implant 1050, the implant 1050 can be further coupled to a marker 1090. The needle 1026 is not limited to a particular type, size, shape, or material. In one instance, the needle 1026 can be a cannula. In one embodiment, the implant 1050 can be suture thread made from any material now known or later developed, including but not limited to catgut, silk, nylon, and polypropylene. The implant 1050 can be absorbable or non-absorbable. The length and diameter of the implant 1050 are not specifically defined, so long as the implant 1050 can be securely fastened in place in a body cavity. In this way, the implant 1050 serves to stabilize a marker 1090, which enables the marker 1090 to serve as a stable target for EBRT in a breast, body cavity or other organ. The marker 1090 is not limited to a specific diameter or shape; for instance, in one embodiment the marker 1090 can be a non-radioactive seed. In another embodiment, the marker 1090 can be round, like a ball. The marker 1090 can be made from any radio-opaque material, including but not limited to ceramic, gold, and titanium. Of note, each implant 1050 can have at least one marker 1090; in other words, multiple markers 1090 can be coupled to each implant 1050, as shown in FIG. 10B. Of further note, multiple implants 1050, each coupled to at least one marker 1090, can be attached in a body cavity. Regardless of the number of implants 1050, an implant 1050 can be used to stabilize any markers 1090 coupled to the implant 1050, so that the markers 1090 can serve as a target for the radiation beam during EBRT. The marker 1090 can be coupled to the implant 1050 in any method now known or later developed. In addition, the marker(s) 1090 can be coupled to the implant 1050 at any position along the implant 1050. Of further note, in another embodiment, the implant 1050 can be radio-opaque with no marker 1090 attached to it;

in other words, the implant 1050 (the suture thread itself) can serve as the target. Of even further note, the needle 1026 along with the implant 1050 can be pushed into tissue by hand or may be loaded, including back loaded, into an applicator, loader, introducer, or other component; in other words, the implant 1050 may be inserted directly into tissue or a body cavity without using another component, such as an applicator, loader, or introducer.

Figure 10C:
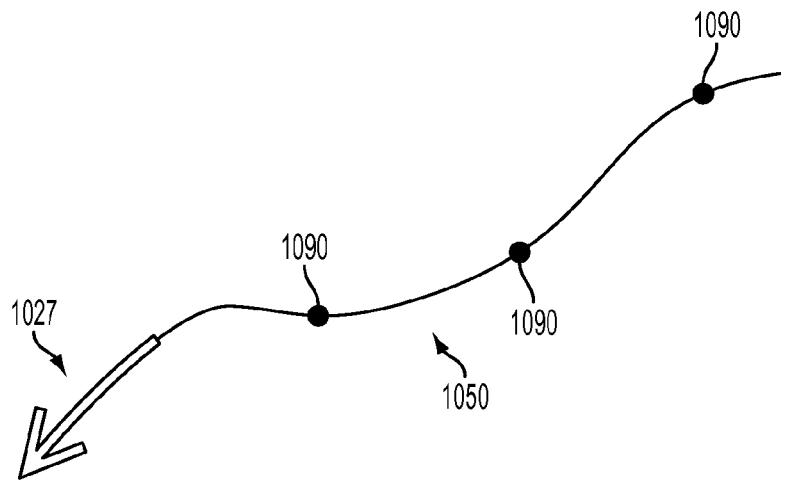

In even further illustration, FIG. 10C is a line drawing of one embodiment of an implant 1050 for use in a radiation targeting system of the present invention can include a barb 1027 coupled to an implant 1050, the implant 1050 can be further coupled to a marker 1090. The barb 1027 is not limited to a particular type, size, shape, or material. Of note, the barb 1027 along with the implant 1050 can be pushed into the tissue by hand or may be loaded, including back loaded, into an applicator, loader, introducer, or other component. In one embodiment, the implant 1050 can be suture thread made from any material now known or later developed, including but not limited to catgut, silk, nylon, and polypropylene. The implant 1050 can be absorbable or non-absorbable. The length and diameter of the implant 1050 are not specifically defined, so long as the implant 1050 can be securely fastened in place in a body cavity. In this way, the implant 1050 serves to stabilize a marker 1090, which enables the marker 1090 to serve as a stable target for EBRT in a breast, body cavity or other organ. The marker 1090 is not limited to a specific diameter or shape; for instance, in one embodiment the marker 1090 can be a non-radioactive seed. In another embodiment, the marker 1090 can be round, like a ball. The marker 1090 can be made from any radio-opaque material, including but not limited to ceramic, gold, and titanium. Of note, an implant 1050 can have no markers 1090 or as shown in FIG. 10C, at least one marker 1090; in other words, multiple markers 1090 can be coupled to each implant 1050, as shown in FIG. 10C. Of further note, multiple implants 1050, each coupled to at least one marker 1090, can be attached in a body cavity. Regardless of the number of implants 1050, an implant 1050 can be used to stabilize any markers 1090 coupled to the implant 1050, so that the markers 1090 can serve as a target for the radiation beam during EBRT. The marker 1090 can be coupled to the implant 1050 in any method now known or later developed. In addition, the marker(s) 1090 can be coupled to the implant 1050 at any position along the implant 1050. Of further note, in another embodiment, the implant 1050 can be radio-opaque with no marker 1090 attached to it; in other words, the implant 1050 (the suture thread itself) can serve as the target.

Of note, in use, following a lumpectomy or other procedure, an implant can be placed into the body cavity during surgery or post-operation under ultrasound guidance or other radiographic modality. After placement of the implant, optionally, the body cavity can be aspirated via the introducer, allowing the cavity to collapse and conform to the size and/or shape of the implant. A radiation beam from an external beam radiation source can then be used to target the implant or any markers coupled to the implant, so radiation therapy can be delivered to the body at the location of the implant or markers. After the completion of the radiation therapy, the implant can be removed from the body under ultrasound guidance or any other radiographic modality.

Having thus described the invention of the present application in detail and by reference to embodiments thereof, it will be apparent that modifications and variations are possible without departing from the scope of the invention defined in the appended claims as follows:

We claim:

1. A target positioning method for external beam radiation therapy comprising:
    positioning a cannula within tissue of a human body;
    transferring an implant in the cannula from the cannula into the tissue of the human body, the implant comprising a single suture thread and at least one marker consisting essentially of a solid single unitary body defining an aperture through which the single suture thread is passed only once prior to the transferring;
    removing the cannula from the human body;
    securing the implant to the tissue by attaching the single suture thread of the implant to the tissue, the secured implant providing a stable target;
    aiming a radiation beam from an external beam radiation source at the at least one marker of the secured implant; and,
    activating the radiation beam subsequent to the securing and aiming.

2. The method of claim 1, wherein transferring the implant in the cannula from the cannula into the tissue of the human body comprises transferring the implant into an organ of the human body.

3. The method of claim 1, wherein transferring the implant in the cannula from the cannula into the tissue of the human body comprises transferring the implant into a tumor in the human body.

4. The method of claim 1, wherein the solid single unitary body is a seed.

* * * * *